United States Patent [19]

Murakami et al.

[11] Patent Number: 4,459,210
[45] Date of Patent: Jul. 10, 1984

[54] POROUS MEMBRANE

[75] Inventors: Eiichi Murakami; Ryozo Hasegawa; Kimihiko Matzuzawa, all of Yamaguchi, Japan

[73] Assignee: Teijin Limited, Osaka, Japan

[21] Appl. No.: 379,698

[22] Filed: May 19, 1982

[30] Foreign Application Priority Data

May 19, 1981 [JP] Japan .................................. 56-74133
Oct. 12, 1981 [JP] Japan ................................. 56-160897
Oct. 13, 1981 [JP] Japan ................................. 56-161965

[51] Int. Cl.$^3$ ............................................. B01D 39/14
[52] U.S. Cl. .................................. 210/500.2; 264/41; 264/178 F; 428/36; 428/398; 521/64; 521/84.1
[58] Field of Search ................. 521/64, 84; 210/500.2; 428/36, 398; 264/41, 178 F

[56] References Cited

U.S. PATENT DOCUMENTS

| | | | |
|---|---|---|---|
| 3,544,489 | 12/1970 | Dowbenko et al. .................. | 521/64 |
| 3,654,193 | 4/1972 | Seiner ................................... | 521/64 |
| 3,655,591 | 4/1972 | Seiner ................................... | 521/64 |
| 3,661,807 | 5/1972 | Seiner ................................... | 521/64 |
| 3,682,848 | 8/1972 | Virnelson .............................. | 521/84 |
| 3,864,289 | 2/1975 | Rendall ................................. | 521/64 |
| 3,950,247 | 4/1976 | Chiang et al. ........................ | 210/640 |

Primary Examiner—Morton Foelak
Attorney, Agent, or Firm—Sughrue, Mion, Zinn, Macpeak and Seas

[57] ABSTRACT

A porous membrane which is composed of cellulose acetate and acrylic polymer, for example, poly(methyl methacrylate) or methyl acrylate-methyl methacrylate copolymer, is highly suitable for plasmapheresis. A polymer alloy consisting of cellulose acetate, acrylic polymer and a small amount of cellulose nitrate has a good spinnability to produce a hollow fiber type membrane and has an excellent biocompatibility.

10 Claims, No Drawings

POROUS MEMBRANE

FIELD OF THE INVENTION

The present invention relates to a porous membrane that is applicable to plasmapheresis and, more particularly, it relates to a porous membrane of a binary or ternary polymer alloy consisting of a hydrophilic cellulose acetate having hydroxyls remaining to be acetylated, an alkyl methacrylate homopolymer or copolymer and, when necessary, cellulose nitrate.

DESCRIPTION OF THE PRIOR ART

Much attention has been paid on the application of a high polymer porous membrane to plasmapheresis, because it can conduct therapeutic plasma exchange more advantageously than the centrifugation. [B.A. Solomon et al; Trans American Soc. Artificial Internal Organs, Vol. 24, 21–26 (1978)] and so on. Gurlant et al have pointed out that the plasma filtration rate and hemocompativility play important roles in the membrane separator for plasmapheresis. ["Therapeutic Plasma Exchange", Springer verlag (1981)]. Further, regenerated cellulose or cellulose acetate has been used as a semi-permeable membrane in hemodialysis, hemofiltration and plasma separation. The material for a medical purpose, differing from the one for such an industrial purpose as reverse osmosis or ultrafiltration, is required to have biocompatibility. From this point of view, it may not be said that cellulose acetate is an ideal material. For example, a cellulose acetate membrane has a tendency to reduce the plasma filtration rate with the purfusion time, because the pores in the membrane are clotted with blood cells ang gigantic molecules of protein. Further, platelets gravely diminish, while blood is subjected to plasmapheretic treatment and extracorporeal circulation. Therefore, despite the porous membrane of cellulose acetate for plasmepheresis was issued by U.S. Pat. No. 3,883,626, improved technology has been desired to improve the hemocompatibility much more.

The object of the present invention is to provide a porous membrane having pores of 0.05 to 1 $\mu$m (micron) size at the peak in the distribution of pore size and a composition suitable for plasmapheresis.

Another object of the present invention is to provide a porous membrane that is in the form of a flat membrane, tubes or hollow fiber.

A further object of the present invention is to provide a method of making a porous membrane. (Summary of the Invention)

The present inventors have found that a porous membrane comprising cellulose acetate and alkyl acrylic polymer is applicable to plasmapheresis. The resultant membrane is used in the form of a thin membrane or hollow fiber. The polymer alloy has high hemocompatibility and advantages of causing more reduced hemolysis and less loss of platelets in the blood, when applied, than a membrane made from cellulose acetate only shows. Moreover, effective pores of 0.2 $\mu$m to 0.6 $\mu$m size are readily formed in the membrane and a thin membrane is given by a conventional method. A hollow fiber membrane is preferably made from a ternary polymer alloy consisting of cellulose acetate-acrylic polymer-cellulose nitrate. The ternary polymer alloy stabilizes the spinning dope, increases spinnability and has good hemocompatibility. (Description of Preferred Embodiment)

The polymer alloy for the porous membrane in the present invention is a binary system of cellulose acetate-acrylic polymer or copolymer or a ternary system of cellulose acetate-acrylic polymer or copolymer-cellulose nitrate.

The cellulose acetate used for the present invention has an acetyl value of 50 to 62 percent as acetic acid and the remaining hydroxyls favorably acts for biocompatibility. A cellulose acetate with a polymerization degree of 80 to 400 is suitably employed in terms of film-forming properties.

The acrylic polymer that can be applied to the present invention is a homopolymer or copolymer containing methacrylic and acrylic esters. Preferable examples of methacrylic ester are methyl, ethyl, n-propyl, iso-propyl, n-butyl, iso-butyl and tert.-butyl esters. Preferable acrylic esters also are methyl, ethyl, n-propyl, iso-propyl, n-butyl, iso-butyl or tert.-butyl one. For example, poly(methyl methacrylate), poly(iso-butyl metharylate), poly(methyl acrylate), poly(-iso-propyl acrylate), methyl methacrylate-methyl acrylate copolymer, methyl acrylate-vinyl pyrrolidone copolymer and iso-butyl methacrylate-iso-butyl acrylate copolymer are preferably used. The acrylic homopolymer or copolymer suitably used for this purpose has molecular weight of about 200 to about 2,000.

In the binary polymer alloy consisting of cellulose acetate and a methacrylic ester polymer or a copolymer thereof, the content of the cellulose acetate is preferably set in the range of from 50 to 95 percent by weight, because the membrane becomes mechanically strong. As the rest part, is used a methacrylic ester polymer.

The solvent for the binary polymer alloy is preferably selected from those which dissolve both cellulose acetate and methacrylic ester polymer. Examples of generally applicable solvents are methylene chloride, acetone, methyl ethyl ketone, ethyl acetate, N-methylpyrrolidone, dimethyl sulfoxide and so on.

In case that the pore size in the porous membrane is required to be 0.1 $\mu$m or more, the solvent is mixed with a non-solvent, which acts as a pore-forming agent. Any organic liquid is used as the non-solvent, if it does not dissolve both polymers. For example hexane, cyclohexane, cyclohexanol, methanol, ethanol, propanol or butanol is preferably used.

In the formation of the membrane, the addition of an inorganic salt to the dope desirably increases the phase separation rate and further expands the pore size.

An ammonium salt, calcium salt, magnesium salt or the like is used as the inorganic salt.

the concentration of the binary polymer alloy in the dope ranges from 5 to 30 percent by weight, preferably from 5 to 20 percent by weight. It is properly set by considering a viscosity easy to form a membrane.

The amount of the non-solvent is 10 to 50 percent by weight, the inorganic salt is 0.5 to 10 percent by weight and the rest is the solvent. When an inorganic salt is employed, the salt is desirably dissolved in methanol and the solution is added to the dope in the range of up to about 10 percent by weight as calcium chloride.

There is no technical difficulty in dissolving these components; however, preferably, both polymers are completely dissolved in the solvent first. When needed, the temperature is raised from room temperature up to 50° C. and the polymers dissolve in about 5 hours.

Then, the non-solvent and the salt solution in methanol are added and stirring is continued for 5 hours to give the clear dope. The process for forming the resultant dope into a porous membrane is basically the same as the general one for wet casting in membrane formation; however, a little difference is caused according to the form of the porous membrane, for example a flat membrane or hollow fiber.

In advance of membrane formation, the dope should be subjected to filtration to remove foreign and insoluble substances. In the process for forming a flat membrane, water or a water-methanol mixture is used as a coagulation bath and the dope is cast. The temperature is preferably 20° C. or lower at which the solvent is hard to vaporize. When necessary, a perforated plate of stainless steel, a glass plate with a smooth solid surface or a rotatory drum is used in the casting.

A hollow fiber membrane is, of course, formed with the binary polymer alloy; however, the use of the ternary polymer alloy is much preferred, which will be mentioned hereinafter.

The solubility parameter of cellulose acetate is 10.9 and polymethyl methacrylate is 10.1. The former is hydrophilic, the latter is hydropholic and the compatibility is poor with each other. However, in the ternary polymer alloy containing cellulose nitrate, the solubility parameter of cellulose nitrate is 10.5 and the compatibility is improved. The resultant ternary polymer alloy gives hollow fiber, for example, by means of the device shown in U.S. Pat. No. 3,724,672 in the same manner as the hollow fiber of cellulose acetate is formed.

The cellulose nitrate used for the ternary polymer alloy has a nitration value of 10.5 to 12.5 percent as nitrogen and a polymerization degree of about 80 to 400. As the cellulose acetate and the alkyl acrylic homopolymer or copolymer are used the polymers having the same properties as those of the cellulose acetate and the acrylic polymer in the binary polymer alloy.

The content of cellulose nitrate in the ternary polymer alloy is in the range of from 0.1 to 10 percent by weight and, in usual cases, the addition by 2 to 4 percent improves the stability of the dope, inhibits the pressure rise during the spinning and enables the continuous spinning for hours. Since the content of cellulose nitrate is low, the resultant porous hollow fiber membrane scarcely shows changes in the pore size and biocompatibility, and can develop the same advantages of the binary polymer alloy characteristically.

As for the composition of the dope, the content of the polymer ranges from 5 to 30 percent by weight, preferably from 5 to 20 percent by weight, the non-solvent from 10 to 50 percent by weight, the inorganic salt from 0.5 to 10 percent by weight and the rest, corresponding to 30 to 60 percent by weight, is the solvent.

The hollow fiber with an average pore size of 0.2 to 0.6 $\mu$m that high hemocompatibility and causes no reduction in filtration rate even after plasma separation for hours has a composition, as a polymer alloy, of 50 to 95 percent by weight of cellulose acetate, 5 to 40 percent by weight of polymethyl methacrylate and 0.1 to 10 percent by weight of cellulose nitrate. Further, to the dope, is added a divalent metal salt such as calcium chloride or magnesium chloride by 0.5 to 5 percent by weight and the concentration of the polymers is adjusted to 12 to 20 percent by weight. Although lowering the concentration of the divalent metal salt has a tendency to make the pore size in the membrane a little smaller, almost no reduction is observed in plasma separation rate but the hemolytic properties are improved. The dope containing higher concentration of the inorganic salt gives a membrane of larger pore sizes. Such a membrane has a high filtration rate at the beginning of use, but the rate decreases with time. Rather, the porous membrane with pore sizes of about 0.2 to 0.4 $\mu$m gives a membrane more suitable for plasmapheresis. When the concentration of the inorganic salt exceeds 10 percent by weight, the pore size becomes remarkably large and the spinnability low to hinder the satisfactory spinning. The reason why the hollow fiber membrane in the present invention is excellent is that blood cells hardly stick to the surfaces and pores and hemolysis scarcely occurs. The proportion of the divalent metal salt in the dope should not be lower than 0.5 percent by weight, because the lower limit of pore size suitable for the plasmapheretic purpose is obtained, when the salt concentration is about 0.5 percent by weight.

In the spinning, the dope is filtered and extruded through the spinneret having an annular nozzle or nozzles. A core agent is simultaneously extruded together with the dope and the extruded dope is subjected to conventional wet- or dry-spinning or combination of semi-dry and semi-wet type spinning. The core agent is required to coagulate the polymer solution gradually and actually, a 1:1 water-methanol mixture, a 1:1:1 water-methanolglycerol mixture or polyethylene glycol of low molecular weight (less than 400) is used.

As the coagulation bath, is used water or a water-alcohol mixture. The temperature of the bath is preferably 30° C. or lower. The extruded hollow fiber is subjected to the semi-dry and semi-wet spinning where the fiber runs in the air about 0.5 cm to 20 cm and comes into the coagulation bath. A chimney is used instead of the air gap or evaporative gap and the chimney depresses the vaporization of the solvent to facilitate the spinning operations.

The flat membrane is practical, when the thickness of about 1 to 100 $\mu$m, preferably 5 to 50 $\mu$m. The hollow fiber membrane is readily spinnable and practical, when the inner diameter is 150 to 500 $\mu$m and the membrane thickness is 5 to 150 $\mu$m.

As for the pore size of the membrane, the distribution is measured by means of a mercury porosimeter, for example, an apparatus made by American Instrument Co. is practical, and the peak value of the distribution curve is given as a representative value of pore size.

The ultrafiltration rate (abbreviated to UFR hereinafter) is determined by measuring the permeation of an aqueous bovin-$\gamma$-globlin solution of 0.05 to 0.2 percent by weight.

The plasma separation rate and hemolysis are observed ex vivo by furnishing a shunt on the carotid artery of a rabbit to conduct the extracorporeal circulation of blood. Plasma is separated with a minimodule that includes a bundle of 200 hollow fibers of 350 $\mu$m inner diameter, 80 $\mu$m membrane thickness and 15 cm (centimeter) length and has 0.03 $m^2$ (square meter) inner surface area to measure the separation rate and the hemolysis. The hemolysis can be observed grossly; however, a spectrophotometer is used to measure the optical density (OD) at 541 nm (nanometer) wave length quantitatively.

EXAMPLE 1

The dope for membrane formation was prepared as follows:

Cellulose acetate of 55% acetyl value and 180 polymerization degree (120 grams) and polymethyl methacrylate of 800 polymerization degree (30 grams) were added to acetone (350 grams) and they were heated at 50° C. for 5 hours to form a clear solution. To the solution, was further added cyclohexanol (300 grams), then ammonium chloride (50 grams) and methanol (150 grams), and stirring was effected thoroughly.

The resultant dope was kept at 20° C. and cast on a glass plate and dipped together with the glass plate in the 1:1 water-methanol coagulation bath to form a flat membrane of 23 μm, thickness.

For the purpose of comparison, cellulose acetate alone was used instead of the polymer alloy to form another flat film of 25 μm thickness through the same procedure.

The UFR of these membranes were measured using water and an aqueous bovine serum γ-globulin solution of 0.2 percent by weight concentration. The results are shown in Table -1 given below. The UFR of the flat membrane made according to the present invention was found to be higher both in water and in the globulin solution.

TABLE I

| Membrane | Membrane thickness (μm) | UFR of bovine globulin solution (ml/m² · hr · mmHg) | γ-globulin sieving coefficient (%) |
|---|---|---|---|
| Polymer alloy | 23 | 9063 | 95 |
| Cellulose acetate | 25 | 7155 | 90 |

EXAMPLE 2

Cellulose acetate of 61% acetyl value and 240 polymerization degree (40 grams) and poly(iso-butyl methacrylate) of 500 polymerization degree (10 grams) were dissolved in methylene chloride (250 grams), then methanol (75 grams), calcium dichloride (25 grams) and cyclohexanol (100 grams) were added to the solution to prepare a dope.

The dope was kept at 20° C. and cast on a glass plate in the methanol coagulation bath to form a membrane. The resultant flat membrane was 27 μm in thickness and showed the UFR given in Table II. The UFR was compared with that of the film consisting of only cellulose acetate. These UFRs were measured in the same manner as in Example 1.

TABLE II

| Membrane | Membrane thickness (μm) | URF of bovine globulin solution (ml/m² · hr · mmHg) | γ-Grobulin sieving coefficient (%) |
|---|---|---|---|
| Polymer alloy | 27 | 3500 | 92 |
| Cellulose acetate | 25 | 2800 | 90 |

EXAMPLE 3

Cellulose acetate of 55% acetyl value and 180 polymerization degree (135 grams) and a 95:5 methyl methacrylate-vinyl pyrrolidone copolymer (15 grams) were dissolved in acetone (250 grams), and methanol (75 grams), borax (25 grams) and cyclohexanone (100 grams) were added to the solution under stirring to prepare a dope.

The dope was kept at lower than 20° C. and cast in the coagulation bath of a 1:1 water-methanol mixture in the same manner as in Example 1 to form a flat membrane of 35 μm thickness. A flat membrane of cellulose acetate of 32 μm thickness was formed in the same way and the UFR was compared with that of the polymer alloy membrane. The result is given in Table III.

TABLE III

| Membrane | Film thickness (μm) | UFR of bovine globulin solution (ml/m² · hr · mmHg) | γ-Globulin sieving coefficient (%) |
|---|---|---|---|
| Polymer alloy | 35 | 3600 | 90 |
| Cellulose acetate | 32 | 2700 | 85 |

EXAMPLES 4-5

A ternary polymer alloy was spun into hollow fiber. Cellulose acetate of 55% acetyl value and 180 polymerization degree (1,150 grams), poly(methyl metharylate) of 800 polymerization degree (300 grams) and cellulose nitrate of 11.5% nitration value and 160 polymerization degree (50 grams) were added to a mixed solution containing cyclohexanol (300 grams), ammonium iodide (500 grams) and methanol (1,500 grams) and they were stirred. Then, acetone (3,500 grams) was added to the mixture and they were heated at 50° C. to form a solution, which was filtered.

The dope and the core agent (aqueous 50 percent by weight methanol solution) were extruded through a spinneret having eight double annular nozzles into the coagulation bath of 1:1 water-methanol that was kept at 25° C. and the resultant filaments were taken up at a speed of 10 meter/min. The hollow fiber was 350 μm in inner diameter and 80 μm in membrane thickness. The spinning was continued for 5 hours; however, any hollow fiber caused no leak at all and the spinning pressure was found to rise little.

The hollow fiber membrane was subjected to ultravilitration test using an aqueous 0.05% γ-globulin solution to determine water permeability and γ-globulin sieving coefficient. The results are given in Table IV as Example 4. Table IV also includes the results on the hollow fiber from a binary polymer alloy containing no cellulose nitrate as Example 5.

TABLE IV

| Polymer alloy | Spinning pressure rise | Leak | UFR of bovine globulin solution (ml/m² · hr · mmHg) | γ-Globulin seiving coefficient (%) |
|---|---|---|---|---|
| Example 4 Ternary | 15 kg/cm² | no | 6,000 | 93 |
| Example 5 Binary (no cellulose nitrate) | 40 kg/cm² | observed | 6,500 | 93 |

EXAMPLES 6-7

Cellulose acetate of 52% acetyl value and 180 polymerization degree (1,200 grams), poly(methyl methacrylate) of 300 polymerization degree (255 grams) and cellulose nitrate of 11.5 percent nitration value and 160 polymerization degree were added to a mixed solution consisting of cyclohexanol (3,000 grams), magnesium chloride (500 grams) and methanol (1,500 grams) and they were stirred. Then, acetone (3,500 grams) was added and they were heated under stirring at 50° C. to form a solution.

In the same way as in Example 4, the dope was filtered and spun into hollow fiber. The resultant hollow fiber had 350 μm inner diameter and 80 μm membrane thickness and these values were the same as in Example 4. This dope also kept stable spinning for hours and was found to give hollow fiber membrane easier than a binary polymer alloy containing no cellulose nitrate, although no difference was substantially found in the performance as hollow fiber between them (Example 7). The results are given in Table V.

TABLE V

|  | Spinning pressure rise | Leak | UFR of bovine globulin solution (ml/m² · hr · mmHg) | γ-Globulin sieving coefficient (%) |
| --- | --- | --- | --- | --- |
| Example 6 | 4 kg/cm² | no | 5,300 | 91 |
| Example 7 | 35 kg/cm² | observed | 5,500 | 91 |

EXAMPLE 8

A ternary composition comprising 77 percent by weight of cellulose acetate of 52 percent acetyl value and 180 polymerization degree, 20 percent by weight of poly(methyl metharylate) of 300 polymerization degree and 3 percent by weight of cellulose nitrate of 11.5 percent nitration value and 160 polymerization degree was used by 165 parts to prepare the spinning dope. Acetone (370 parts) as a solvent, methanol (140 parts) and caprolactone (300 parts) as non-solvents and calcium chloride as a poring agent were mixed and the above polymer composition was added to the mixture to prepare the spinning dope.

At this time, the concentration of calcium chloride was made to vary, based on the dope, to about 5 percent (50 parts), about 3.5 percent (35 parts), 2.5 percent (25 parts) and about 0.8 percent (8 parts) (where the amount of the solvent mixture was changed according to the amount of calcium chloride so that the proportion was kept constant, 83.5 percent in total) to measure the pore size, UFR, plasma separation performance and hemolyzation of the hollow fibers. [Run Nos. A through D]

The dopes were extruded through annular nozzles into the 1:1 water-methanol coagulation bath and simultaneously a 1:1:1 water-methanolglycerol solution was injected into the inside of the hollow fiber as a core agent. The fiber was rinsed and would at 8.5 meter/minute. The resaltant hollow fiber had 350 μm inner diameter and 80 μm membrane thickness. The results are shown in Table VI.

TABLE VI

| Run Nos. | CaCl₂ concentration (%) | Peak of pore distribution (μm) | UFR (ml/m² · hr · mmHg) | Plasma separation rate (ml/m² · hr · mmHg) | Hemolysis OD₅₄₁ |
| --- | --- | --- | --- | --- | --- |
| A | 5 | 0.6 | 6,000 | 57 | 0.83 |
| B | 3.5 | 0.45 | 4,000 | 65 | 0.43 |
| C | 2.5 | 0.35 | 1,500 | 75 | 0.10* |
| D | 0.8 | 0.20 | 700 | 50 | 0.10* |

Note: *0.10 is a value showing substantially no hemolysis.

The results in Table VI show that there are tendencies to increase hemolysis, when the concentration of calcium chloride exceeds 3.5 percent in the dope and to lower the plasma separation rate as the concentration of calcium chloride becomes lower. Consequently, the concentration of the inorganic salt is suitably in the range from 1 to 3 percent by weight in the dope.

EXAMPLE 9

The amount of calcium chloride was made to vary in the dope as shown in Example 8 to form hollow fiber membranes with pores different in sizes. A composition comprising cellulose acetate (75 percent by weight), poly(methyl methacrylate) (22 percent by weight) and cellulose nitrate (3 percent by weight) was made into hollow fiber membrane of 250 μm inner diameter and 75 μm membrane thickness and 200 filaments of the hollow fiber were bundled to form a minimodule of 15 cm length, which was used as a plasma separator. The separator had 0.03 m² inner surface area. It was rinsed with physiological saline and perfused with physiological saline containing 500 Unit/l heparin before used.

In an animal test, a shunt of silicone rubber tube was set between the carotid artery and the cervical vein of a white rabbit of about 3 kilogram body weight and plasma separation was conducted under anesthetization with thiopental for three hours. At the beginning of blood perfusion, 1000 units of heparin was injected; however, it was discontinued since then. The blood flow rate was set to 15 ml/min and the preliminary extracorporeal perfusion was continued for 15 minutes. The separated serum was sent back to the body with a blood pump.

The results of three hollow fiber modules differing in pore size (Runs E, F and G) are given in Table VII on UFR, plasma filtration rate and hemolysis.

TABLE VII

| Runs | Peak of pore size distribution (μm) | The oroperties of the polymer alloy hollow fiber membranes | | |
|---|---|---|---|---|
| | | UFR of bovine-globuline in 0.05 % sol (ml/m² · hr · mmHg) | Plasma filtration rate (ml/m² · hr · mmHg) | Hemolysis Hb in plasma (mg/de) |
| E | 0.6 | 6,000 | 57 | 700 |
| F | 0.35 | 2,000 | 65 | 350 |
| G | 0.2 | 1,000 | 75 | 157 |

The hollow fiber membrane made from the polymer alloy according to the present invention showed 20 percent to 50 percent higher plasma filtration rate than that of polypropylene hollow fiber with the peak of pore size at 0.7 μm (the filtration rate of polypropylene membrane was 50 ml/m².hr.mmHg). Further, the polymer alloy was on the same level in blood protein sieving coefficient as that of polypropylene membrane. During the extracorporeal perfusion, the reduction of platelet in blood was observed between the inlet and outlet of the plasma separator; however, the membrane of the polymer alloy according to the present invention was superior to that of polypropylene or cellulose acetate to cause less reduction in platelet. The results are given in Table VIII.

TABLE VIII

| Perfusion time (min.) | Percent losses of platelet in blood in hollow fiber membranes | | |
|---|---|---|---|
| | Polymer alloy | Cellulose acetate | polypropylene |
| 20 | −24 | −56 | −4 |
| 40 | −17 | −57 | −26 |
| 60 | −5 | −46 | −26 |
| 120 | ±0 | −6 | −24 |
| 180 | ±0 | +3 | ±0 |

The polymer alloy according to the present invention took about 1 hour for platelet recovery, whereas cellulose acetate 2 hours and polypropylene 3 hours. The little reduction in platelet also is one of excellent features.

As cited above, the hollow fiber membrane of the polymer alloy according to the present invention is readily formed, reduces the adhesion of blood platelet and shows high filtration performances, thus it is concluded that it is excellent as a plasma separation membrane.

What is claimed is:

1. A porous membrane for use in plasmapheresis, comprising cellulose acetate and acrylic ester polymer or comprising cellulose acetate, acrylic ester polymer and cellulose nitrate, and, wherein said membrane for use in plasmapheresis has the peak in the pore size distribution at 0.05 to 1 μm.

2. A porous membrane according to claim 1 wherein the cellulose acetate has 50 to 62 percent by weight of acetyl value as acetic acid and a polymerization degree of 80 to 400.

3. A porous membrane according to claim 1 wherein the acrylic polymer is selected from the group consisting of homopolymers or copolymers of methyl acrylate, ethyl acrylate, propyl acrylate, butyl acrylate, methyl methacrylate, ethyl methacrylate propyl methacrylate and butyl methacrylate.

4. A porous membrane according to claim 1 wherein the cellulose nitrate has a polymerization degree of 80 to 400 and 10.5 to 12.5 percent by weight of nitration value as nitrogen.

5. A porous membrane according to claim 1 which is in the form of a sheet, tube or hollow fiber.

6. A process for producing a porous membrane for use in plasmapheresis, comprising casting, inclusive of spinning, a dope comprising:
   (a) 5 to 30 weight percent of polymer alloy, comprising cellulose acetate and an acrylic ester polymer or comprising cellulose acetate, acrylic ester polymer and cellulose nitrate
   (b) 30 to 60 weight percent of solvent,
   (c) 10 to 50 weight percent of non-solvent, and
   (d) 0.5 to 10 weight percent of inorganic compound,
and coagulating the dope with the use of water or a mixture of water and one or two monohydric, dihydric, or trihydric alcohols, and rinsing with water, and, wherein said membrane for use in plasmapheresis has the peak in the pore size distribution at 0.05 to 1 μm.

7. A process of claim 6 wherein the polymer alloy consists of 50 to 95 weight parts of cellulose acetate, 0.1 to 10 weight parts of cellulose nitrate and 5 to 40 weight parts of acrylic polymer.

8. A porous membrane according to claim 1 wherein the acrylic polymer is selected from the group consisting of homopolymers or copolymers of methyl methacrylate, ethyl methacrylate, propyl methacrylate and butyl methacrylate.

9. A porous membrane in the form of hollow fiber according to claim 5 wherein the inner diameter is 150 to 500 μm and the membrane thickness is 5 to 150 μm.

10. The process of claim 6 wherein the concentration of the inorganic compound in the dope is in the range of 1 to 3 percent by weight.